United States Patent
Zilker, Jr. et al.

(10) Patent No.: US 6,592,827 B1
(45) Date of Patent: Jul. 15, 2003

(54) SAMPLING SYSTEM FOR FLUIDIZED BED GAS PHASE POLYMERIZATION REACTION SYSTEMS

(75) Inventors: Daniel Paul Zilker, Jr., Charleston, WV (US); Christopher Scott Hunnisett, Dunbar, WV (US); Donald Robert Fields, Nitro, WV (US); Kiu Hee Lee, So. Charleston, WV (US)

(73) Assignee: Univation Technologies LLC, Houston, TX (US)

( * ) Notice: Subject to any disclaimer, the term of this patent is extended or adjusted under 35 U.S.C. 154(b) by 0 days.

(21) Appl. No.: 09/694,852

(22) Filed: Oct. 24, 2000

(51) Int. Cl.[7] ................. G05D 16/00; G05D 1/00; G01N 1/00; G05B 17/00; F16K 31/02
(52) U.S. Cl. ............. 422/119; 422/81; 422/105; 422/112; 422/116; 73/23.41; 251/129.01
(58) Field of Search ............. 422/62, 63, 79–81, 422/103, 105, 112, 116, 119; 73/23.36, 23.41; 251/328, 129.01

(56) References Cited

U.S. PATENT DOCUMENTS

| | | | | |
|---|---|---|---|---|
| 4,361,538 A | * | 11/1982 | Dicoi et al. ............. | 422/62 |
| 4,668,476 A | * | 5/1987 | Bridgham et al. ............. | 422/62 |
| 5,126,274 A | * | 6/1992 | McIver et al. ............. | 436/140 |
| 5,218,996 A | * | 6/1993 | Schmitt-Matzon ..... | 137/596.17 |
| 5,224,684 A | * | 7/1993 | Schouten ............. | 251/30.05 |
| 5,627,328 A | * | 5/1997 | Sheridan et al. ......... | 73/863.83 |
| 5,730,937 A | * | 3/1998 | Pardikes ............. | 422/62 |
| 5,993,747 A | * | 11/1999 | Mandel ............. | 422/119 |
| 6,260,822 B1 | * | 7/2001 | Puranik ............. | 251/328 |

FOREIGN PATENT DOCUMENTS

EP     1 099 473 A1  *  5/2001

* cited by examiner

Primary Examiner—Glenn Caldarola
Assistant Examiner—Douglas W. Rudnick
(74) Attorney, Agent, or Firm—Univation Technologies LLC

(57) ABSTRACT

There is provided an automated sampling system for taking polymer samples from a fluidized bed, gas phase reaction system which utilizes at least one volatile, hazardous monomer. The sampling system provides minimal sample-to-sample variability, improved reactor control and polymerization operability which minimizing potential exposure or release of the volatile, hazardous monomers.

10 Claims, 2 Drawing Sheets

EPR-1 Commercial Reactor Sampling System

Figure 1. Automated Sampling System
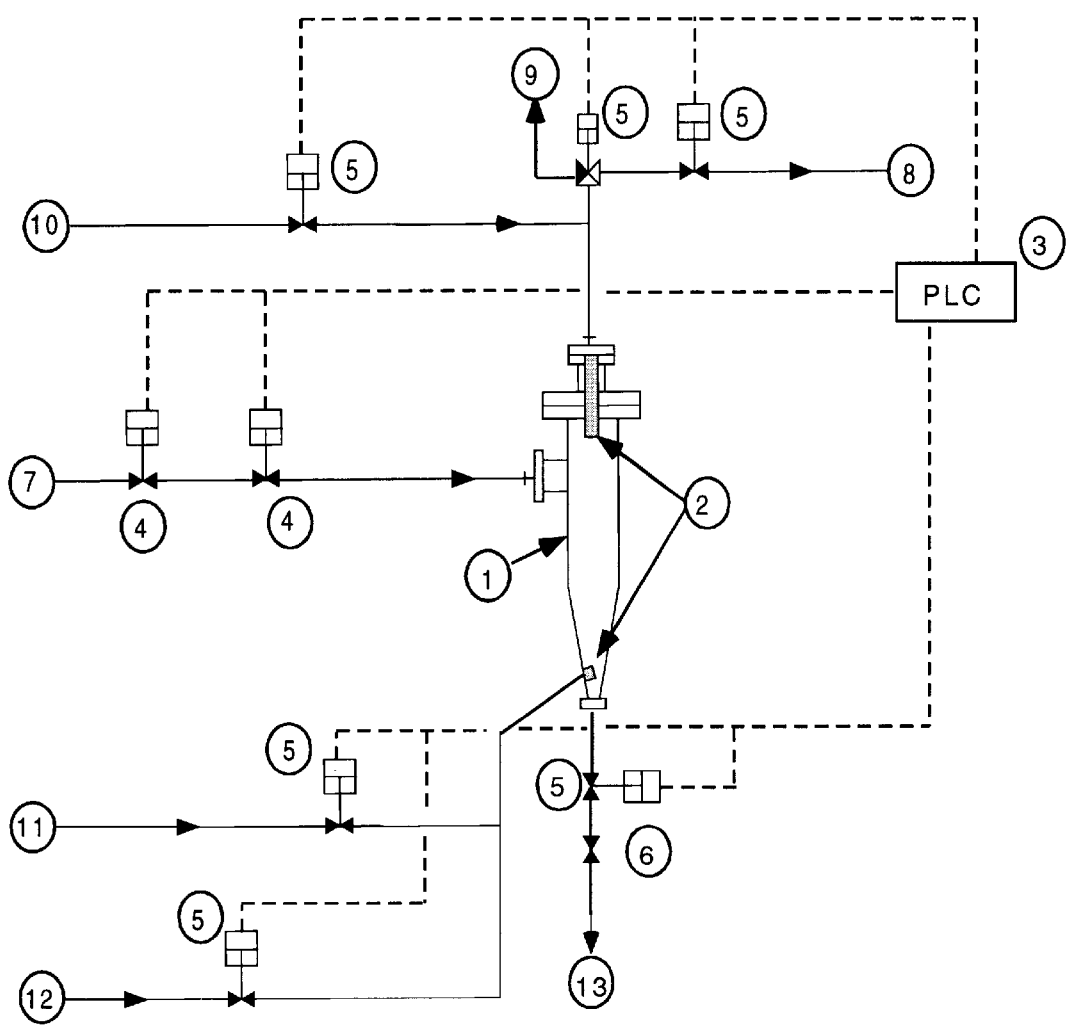

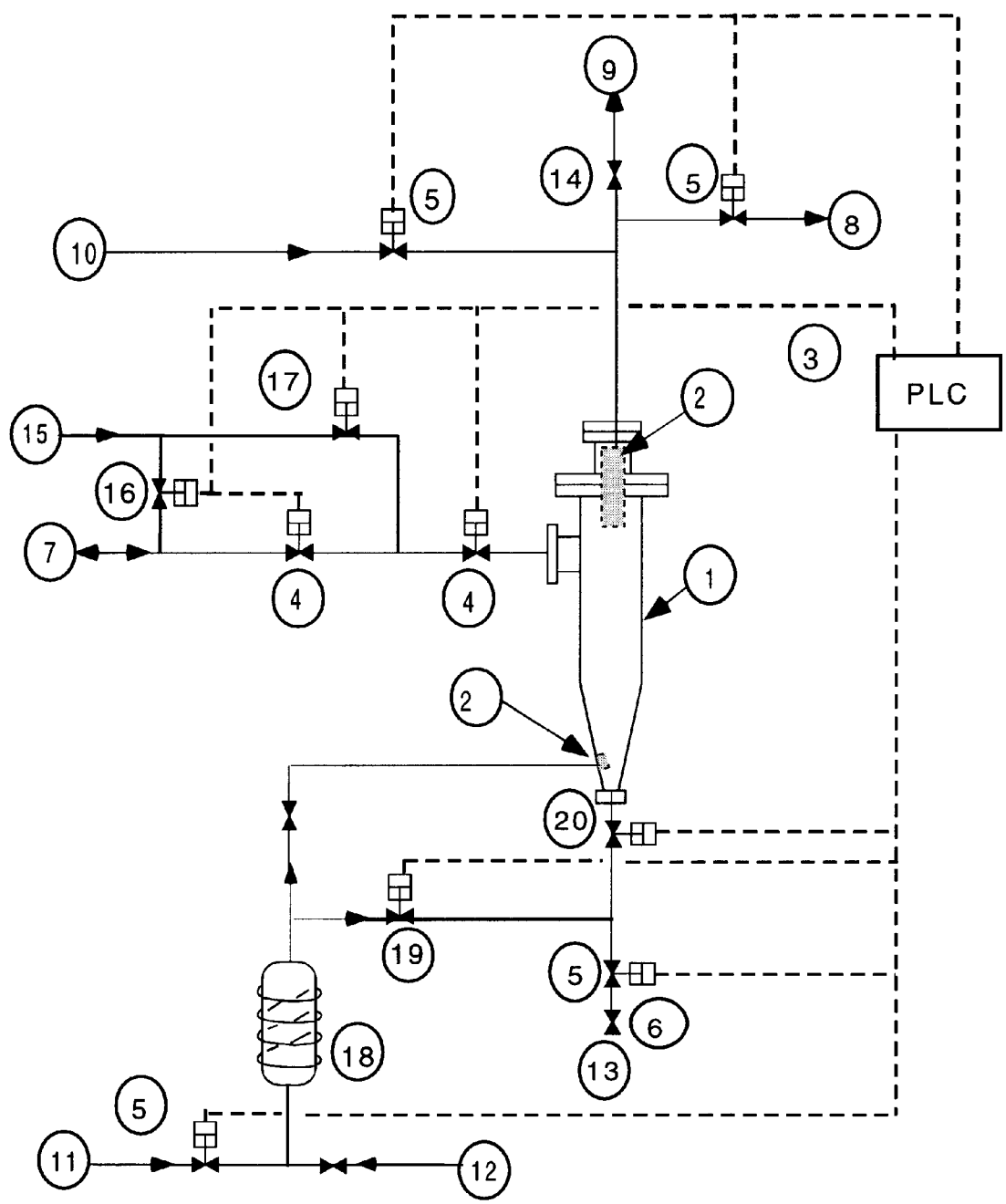
Figure 2. EPR-1 Commercial Reactor Sampling System

SAMPLING SYSTEM FOR FLUIDIZED BED GAS PHASE POLYMERIZATION REACTION SYSTEMS

FIELD OF THE INVENTION

The invention relates the production of a polymer in a gas phase, fluidized bed polymerization. More particularly, the invention relates to a sampling system for such a gas phase polymerization of a polymer (such as PE, PP, and/or a sticky polymer such as an EPR).

BACKGROUND OF THE INVENTION

The physical and chemical properties of the product being produced in a continuous gas phase reactor with a fluidized bed must be determined to ensure the product remains within specification. Ideally, these properties should be measured in-situ, but reliable technology has not been developed to accomplish this goal. Therefore, product samples need to be taken and analyzed externally to the reactor. Generally such samples are taken in conveying lines after the reactor.

When this is done, some time lag is introduced depending on the equipment between the reactor and the sample point and the residence times in that equipment. Taking samples from conveying lines or downstream of pressure-rated product discharge tanks has been the norm.

Cyclones have been used to separate the conveying gas from the solids. These systems work reasonably well for polymers (e.g., crystalline alpha olefin polymers) where the monomers are not too hazardous and can be easily purged. (Cyclones would probably not work well for sticky polymers)

However, the advent of gas-phase processes for sticky polymers such as ethylene-propylene rubbers (EPR), including ethylenepropylene-diene elastomers, and butadiene rubbers (BR) makes these simple samples systems useless due to the hazard ratings of the monomer (i.e., the diene). EPR products contain (ethyldiene norbornene (ENB) and BR products contain 1,3-butadiene which have stringent controls to limit air emissions and human exposure. ENB has a strong odor which can be detected in ambient air at 13 ppbv. The current exposure limit for 1,3-butadiene is only 1 ppmv.

Accordingly, there is an on going need to obtain safe, reliable sampling of such polymerizations.

SUMMARY OF THE INVENTION

Surprisingly, the present invention provides a process and apparatus for sampling during the polymerization of a sticky polymer.

There is provided a process for sampling a polymer during its production in a gas phase fluidized bed reactor comprising:
(1) analyzing a sample containment vessel for leaks from the sample containment vessel to the environment and for leaks from the reactor to the sample containment vessel;
(2) removing a sample of polymer from the fluidized bed to the sample containment vessel;
(3) contacting the sample of polymer with an aluminum alkyl quenching agent;
(4) purging the sample of polymer in the sample containment vessel with an inert gas; and
(5) discharging said sample of polymer from the sample containment vessel.

There is further provided an apparatus comprising:
(1) a pressure rated sampling vessel with a conical discharge bottom wherein the cone angle is sufficiently steep to prevent sticky solids from easily bridging the bottom of the vessel;
(2) one or more filters to keep a solid product inside the sampling vessel and prevent it from migrating to instrumentation or to other process streams;
(3) a programmable logic controller (PLC) which can sequence the operation of the valves and perform logic tests in conjunction with other process instrumentation including pressure, temperature, and flow sensors ensuring the sampling system is operating safely and is performing the desired functions;
(4) one or more full-bore PLC-controlled remotely actuated valves connected to the reactor with metal seats that minimize leaks from the reactor into the sampling vessel;
(5) one or more PLC-controlled remotely actuated valves connected the sampling vessel to other process streams such as purge gas, quench agent, vent, flare, reactor cycle gas, or to discharge the product; and
(6) a manual discharge isolation valve allowing control of the final discharge of the product into the sample container for off-line analysis.

BRIEF DESCRIPTION OF THE DRAWINGS

FIG. 1 is a schematic drawing of an automated sampling system of the invention. FIG. 2 is a depiction of a commercial EPR reactor sampling system of this invention. In FIGS. 1 and 2:

1=Pressure-rated conical bottom sampling vessel
2=Filters internal to sampling vessel, typically sintered metal filter media with a 1-10 micron pore size
3=Programmable logic controller (PLC), e.g. Texas Instruments Model 405
4=Full-bore metal seated PLC-controlled remotely actuated valve, typically a ball valve
5=PLC controlled remotely actuated valve, typically a ball valve
6=Full bore manual actuation valve, typically a ball valve.
7=Reactor
8=Flare
9=Atmospheric Vent
10=Nitrogen
11=Heated nitrogen
12=Alcohol
13=Sample Discharge Container for Off-line analysis
14=Manual Atmospheric Vent Valve (FIG. 2 only)
15=Reactor Cycle Gas (FIG. 2 only)
16=PLC-Controlled Remotely-Actuated Cycle Gas Purge Valve (FIG. 2 only)
17=PLC-Controlled Remotely-Actuated Cycle Gas Sample Line Purge Valve (FIG. 2 only)
18=Steam Traced Alcohol Vaporization Vessel (FIG. 2 only)
19=Heated Nitrogen/Alcohol Addition PLC-Controlled Remotely-Actuated Valve (FIG. 2 only)
20=Upper Full-Port PLC-Controlled Remotely Actuated Discharge Valve (FIG. 2 only)

DETAILED DESCRIPTION OF THE INVENTION

EPR and BR polymers may cross-link or make very high molecular weight polymers if the polymerization reaction is not terminated. The ideal sample system for EPR and BR polymers would be one that can not only take a sample directly from the reactor but it could also perform purging and reaction termination operations rendering the sample innocuous to operating personnel. No sample system capable of performing these functions was known to the authors prior to the development of this process and apparatus.

An apparatus of the invention has been developed for taking polymer samples from a fluidized bed gas phase reaction system which is capable of handling volatile hazardous monomers such as 1,3-butadiene. The apparatus consists of a small conical bottom vessel which is connected directly to a fluidized bed gas phase reactor. The vessel contains internal filters that prevent product fines from exiting the system and protect instrumentation and vent lines from being plugged with product. Special metal-seated valves are used to isolate the sampling vessel from the process. A programmable logic controller (PLC) sequences the operation of the valves attached to the vessel to obtain a sample of the polymer. The PLC logic also ensures the sampling vessel is leak-free, purges the sampling vessel with inert gas, controls the sample size, removes the sample, purges the sample free of monomer with inert gas, chemically passivates the sample, and then permits the discharge of the sample into a container for removal. The PLC logic controls the duration of the purging sequence while ensuring the purge gas flowrate and temperature are maintained during the purging process.

The automation of the sampling process using the aforementioned vessel and PLC logic ensures that every sample experiences the same conditioning prior to analysis. This decreases sample-to-sample variability which improves reactor control and operability. The sampling system minimizes the potential for exposing operating personnel to hazardous monomers and reaction by-products. The purged and passivated sample is analyzed off line to determine product properties and physical/chemical characteristics. Results from the analyses of the sample are used to guide adjustment to reaction conditions.

The invention is an apparatus comprising means for automatically taking a sample from a gas phase fluidized bed reactor that also purges the sample to remove hydrocarbons and contacts the sample with reaction gel inhibitors or other compounds. The apparatus is comprised of a conical bottom pressure-rated sample chamber, remotely actuated valves, pressure transmitters, pressure indicators, flow indicators, flow restriction orifices, valves, check valves, filter elements, and a programmable logic controller (PLC). The programmable logic controller (PLC) sequences the operation of the valves and performs logic tests to ensure the safe operation of the sampling system and to provide operating personnel with trouble shooting information which is transmitted by to a digital control system for annunciation on operating display units. The remotely operated tasks the PLC could be performs could be done manually but sample reproducibility and safety would be sacrificed. The sampling apparatus is well suited for taking samples from highly reactive and toxic reaction environments and discharging a sample which can be readily handled by operating personnel. The sampling system minimizes exposure of operating personnel to materials with low permissible exposure levels and minimizes the emission of toxic materials to the environment. Each sample taken by the automated sampling system receives the same treatment eliminating the bias that may be created by manually attempting to perform the same tasks involved in taking a sample repeatedly. The sample system may be cycled through its processing steps repeatedly as necessary to obtain samples as analytical testing requirements dictate.

A simplified drawing of the pilot plant automated sampling system is shown in FIG. 1. Its primary components consist of a conical bottom pressure-rated cylindrical conical bottom sampling vessel (1), filter elements (2), a programmable logic controller (PLC) (3), full-bore remotely actuated valves with metal seats (4), remotely actuated valves (5), and a manually actuated full-bore discharge valve (6). The PLC sequences the operation of the actuated valves and performs logic tests necessary for the safe operation of the sampling system. The design of the sample vessel (1) includes a conical bottom with conical angle of at least 45 degrees to enable the flow of solid polymer samples into the sample collection container and is designed for unlimited cycles in cyclical pressure service. Steeper angle cones are routinely used to aid the flow of solids from the vessel. The sampling vessel (1) routinely experiences abrupt changes in internal pressure from near atmospheric pressure to pressures as high as 600 psig and back to near atmospheric pressure during its routine operation.

The reactor port which conveys product from the reactor (7) into the sampling vessel (1) through the full-bore remotely actuated valves (4) is normally within a few inches vertically of the gas distributor plate in the pilot plant fluidized bed reactors and at the same height as the normal product discharge nozzle. The use of full-port ball type valves with metal seats is recommended for product transfer valves (4). Although both valves are not necessary, the second valve provides better isolation of the sample vessel (1) from the reactor (7) should one of the valves develop a leak. The product transfer valves are close coupled to the reactor, preferably using a reactor boss instead of a normal flange outlet to minimize the dead volume between the reactor and the product transfer valve closest to the reactor. A similar sampling system is also being used which removes solid product samples from the product discharge vessel connected to the reactor instead of taking the product sample directly from the reactor.

A sampling sequence begins by operating personnel requesting a sample electronically via the programmable logic controller (PLC)(3). All remotely actuated valves begin in the closed position and the PLC checks to ensure the initial valve positions are correct. If any step in the sampling procedure is in error, the PLC activates a fail-safe response. This response is for the logic to alert operating personnel, bypass the remaining sampling steps, and return all remotely actuated valves to their fail safe positions.

After the initial valve position check, the PLC then checks the pressure in the sampling vessel. If the pressure exceeds 15 psig, gas inside the sampling vessel (1) is vented via removed actuated valves (5) to the flare (8). The vented gas could also be sent to a catalytic oxidizer or similar device to prevent emissions of hydrocarbons to the environment. The pilot plant sampling system uses a remotely actuated 3-way valve (5) to direct the vented gas from the sampling vessel to the atmosphere (9) or to the flare (8). This additional valve is not necessary if the vented gas is sent to an emission reduction device which operates at low pressure such as a catalytic oxidizer.

If the pressure in the sample chamber does not vent below 15 psig within a specified time (30 seconds), a system error occurs which results in the aforementioned fail safe response. Being unable to vent the sample vessel may indicate a leak from the process into the sample vessel through a faulty valve or that the vent line is blocked.

The next step the apparatus performs is to check for leaks from the sampling vessel (1) to the environment or leaks from the process into the sampling vessel. The sampling vessel is pressurized with nitrogen (10) to approximately 150 psig through a remotely actuated valve (5) and then isolated from the pressurization source. A restriction orifice is used in the pilot plant to control the sampling vessel pressurization rate. Assuming the reactor pressure is greater than 150 psig and the pressure inside the sampling vessel continues to rise, it may be indicative of.a leak from the reactor (7) to the sampling vessel (1) through faulty valves (4). In this case, the sampling systems fail-safe response is activated. If the pressure inside the sample system decreases below a prescribed limit which indicates a leak to the environment, the fail-safe response is activated by the PLC.

After successfully passing the sampling vessel pressure check, the sampling vessel is cyclically pressure purged with nitrogen and vented to remove possible contaminants. The nitrogen is vented to flare at the end of each pressurization cycle. The number of pressurization-vent cycles is variable but six are typically performed in the pilot plant. This step is not absolutely necessary but it may minimize the amount of residual oxygen and moisture in the sampling vessel that migrates into the reactor when a sample is taken.

The PLC pressurizes the sampling vessel (1) to control the size of the sample taken from the reactor. The lower the differential pressure between the reactor and the sample vessel, the smaller the sample. Although the control of sample size is not precise, the pressure in the sample vessel can usually be adjusted to keep the sample size within a few hundred grams. This step is not necessary if the user is not concerned with sample size or chooses to have the size of the sampling vessel control the sample size.

The sample transfer valves (4) open which allow solids to flow from the reactor into the sampling vessel. An electro-pneumatic interlock in addition to PLC logic is also used to ensure that the product transfer valves (4) can not be open at the same time as the remotely actuated discharge valve (5) on the bottom of the sampling vessel. The PLC monitors the sampling vessel pressure during this transfer. If no increase in sampling vessel pressure occurs, the transfer line from the reactor to the sampling vessel is assumed to be plugged and the PLC alerts operating personnel and the fail-safe response is activated. The solids are allowed to settle for a few seconds before the pressure is vented from the sampling vessel. Filters (2) inside the sampling vessel contain the solids within the vessel and protect the instrumentation leads to the pressure transmitters from being plugged with the solids. Sintered metal filters are typically because of their mechanical strength.

Once the sample is inside the sampling apparatus, the gaseous contents of the sampling vessel are vented to the flare through a filter (2). A restriction orifice is installed on the vent line in the pilot plant to prevent too rapid a depressurization from lifting the solids into the upper portion of the sampling vessel. The upper filter on the sampling vessel vent is located above the solids entry port to prevent solids from directly impacting on the filter when the sample is transferred from the reactor to the sampling vessel. The PLC monitors the depressurization step and activates the fail-safe response if the sampling vessel pressure does not decrease to less than 15 psig within 30 seconds. While the sampling vessel is being vented, the remotely actuated valve connected to the flare is closed briefly and the filter is blown back with nitrogen to clean it before the next sample is taken. Heated nitrogen (11) at a temperature of 40–80° C. at a flowrate of approximately 20 lb/hr is then passed through the bottom internal filter into the sampling vessel. This gas purges volatile hydrocarbons from the solid sample and is vented to the flare. The PLC monitors the flow rate and temperature of the hot nitrogen purge stream. A timer inside the PLC controls the duration of the purge flow. If the purge flow or its temperature is not within prescribed limits, the timer stops and alarms operating personnel. The timer stops until the flow and temperature are within their prescribed limits.

Shortly after the initiation of the purge flow, alcohol (12) is slowly metered into the hot nitrogen gas stream. Methanol, ethanol, and isopropanol have been used in the pilot plant. Other substances with similar vapor pressures could also be used. Alcohol reacts with the cocatalyst which terminates any subsequent reaction in the sampling vessel. Alcohol also prevents the formation of gels and of other high molecular weight species. The flowrate of alcohol is regulated by a fine capillary on one sampling system in the pilot plant. In another nearly identical sampling system, the hot nitrogen steam is passed through a small vessel containing alcohol where the alcohol-enriched stream leaving the vessel is sent to the sampling vessel. Both methods have been shown to be effective at quenching the cocatalyst residue in the sample and in eliminating gel formation.

In the capillary system, the PLC controls the duration of the alcohol injection. The molar ratio of alcohol used in the sampling system is at least at a 1:1 mole ratio to the cocatalyst. Typically, a 5:1 alcohol/cocatalyst mole/mole ratio is used in the pilot plant to ensure an adequate quench and to account for a less than ideal distribution of gas flow within the sampling vessel. Alcohol to cocatalyst mole ratios as high as 30:1 have been used. Alcohol quenching may not be necessary for some catalyst systems.

After the sample is purged and quenched, the residual pressure inside the sampling vessel is vented to the flare. When the pressure drops below 2 psig, the contents are ready to be discharged and a logic permissive allows the remotely actuated discharge valve (5) on the bottom of the sampling vessel to be opened. In the pilot plant, the measurements from two redundant pressure transmitters are used to ensure the pressure in the sampling vessel is low enough to allow the remotely actuated discharge valve to open. At this stage in the process after completing all the required sample purging and quenching with alcohol, the PLC vents the pressure inside the sampling vessel to the atmosphere when the sampling vessel pressure falls below 5 psig. Pressure in the pilot plant flare system would sometimes prevent the sampling vessel pressure from dropping to 2 psig thereby inhibiting the product discharge logic. A manual full-bore discharge valve (6) is installed in the pilot plant sampling system to further minimize emissions and to give operating personnel some control of the discharge rate of the solids into the sampling container (13). Once the sample is removed, the sampling system is ready to take another sample by repeating the same tasks.

The sampling procedure in the commercial system (FIG. 2) is very similar and only the differences will be noted. The commercial sampling apparatus performs the same vessel integrity and pressure purging as the pilot plant automatic sampling system. The 3-way remotely actuated valve (5) which selects between the flare (8) and an atmospheric vent (9) in FIG. 1 is replaced by a manual valve (14) on the atmospheric vent header in the commercial system in FIG. 2. In the commercial sampling apparatus, a differential pressure transmitter is used to adjust the pressure difference between the reactor (7) and the sample vessel (1) immediately prior to taking a sample to control the size of the sample. In the pilot plant system, the operating technicians adjust the pre-sampling pressure inside the sampling vessel to control the sample size rather than directly adjusting a differential pressure. The end result is the same being that the sample size is controlled by the differential pressure between the reactor and the sampling vessel.

Another significant difference is that the commercial facility uses cycle gas (15) flow to keep the reactor port clear of solids between samples through remotely actuated valve (16) in FIG. 2. A 60 fps minimum gas velocity is recommended to keep the port clear and to keep solid saltation from occurring. However, the velocity is the EPR-1 unit is probably no better than 10–20 fps. The differential pressure between the discharge of the compressor and the reactor bed at the sampling port provides the motive force for the cycle gas. Once the apparatus passes its integrity check, is pressure purged with nitrogen, and pressurized to the proper differential pressure, the sampling procedure begins by closing the cycle gas purge valve (16). Then the metal seated full-port product transfer valves (4) open to allow solids to flow into the sampling vessel. The remotely actuated product transfer valve (4) attached to the reactor closes and the cycle gas purge pressure via remotely actuated valve (17) is used to push into the sampling vessel. The other remotely actuated full-port valve (4) connected to the sampling vessel (4) closes along with the purge gas valve(17). The purge gas flow is turned back on to the reactor sample port by opening the sample gas purge valve (16). The cycle gas purge flow is maintained until the next system is ready to take the next sample from the reactor.

Sample purging is nearly identical to the pilot plant apparatus where heated nitrogen is passed through a small vessel containing alcohol (18). One difference is that the alcohol-rich stream may be fed either through a filter located on the bottom side of the conical section or it may be fed via another remotely-actuated valve (19) into the discharge piping beneath the sampling vessel between the two-port remotely actuated discharge valves on the bottom of the sampling vessel. The upper remotely actuated full port discharge valve (20) is not used in the pilot plant sampling system and was added in the commercial system because the lower filter (2) in the plant sampling vessel continued to plug. Higher reactor operating pressures at the EPR-1 vs the pilot plant may have caused this filter problem. When a solids sample is transferred from the reactor into the sampling vessel at EPR-1, the purge gas is completely isolated from the sampling vessel by valve (20). In the pilot plant, the only protection for the purge gas is the filter itself.

The discharge sequence for the apparatus at the EPP-1 and the pilot plant are similar with identical logic permissives that must be met before the remotely actuated discharge valves (20) and (5) on the bottom of the sampling vessel will open. PLC logic and an independent external triple redundant PLC ensures that product transfer valves (4) as well as cycle gas purge valve (17) are not open at the same time as the remotely actuated discharge valves. A manual discharge valve (6) on the bottom of the sampling apparatus is used by operating technicians to control the flow of solids into the sample container (13). Once the purged and quenched sample is removed from the apparatus, the automated sample system is ready to take another sample.

The location of the nozzle chosen for the sampling system in the commercial unit is more important compared to the pilot plant. It has been recommended that the sampling port be above the gas distributor plate away from the fluid mechanical influences of the gas jets immediately above the plate. The current port for the commercial sampling system is only a few inches above the plate which makes it more sensitive to larger agglomerates and less sensitive to fines. It may also be necessary to add an insert to the sampling nozzle to allow the sampling system to take a sample a short distance away from the wall of the reactor. The EPR-1 commercial unit has not implemented these changes to ensure the sample is truly representative of the fluidized bed contents.

Polymerization Processes and Conditions.

The present invention is not limited to any specific type of stirred or fluidized gas phase polymerization reaction and can be carried out in a single reactor or multiple reactors (two or more reactors preferably connected in series). In addition to well-known conventional gas phase polymerizations processes, "condensed mode", including the so-called "induced condensed mode", and "liquid monomer" operation of a gas phase polymerization reactor can be employed.

A conventional fluidized bed process for producing resins is practiced by passing a gaseous stream containing one or more monomers, usually one monomer, continuously through a fluidized bed reactor under reactive conditions in the presence of a nickel catalyst. Product is withdrawn from the reactor. A gaseous stream of unreacted monomer is withdrawn from the reactor continuously and recycled into the reactor along with make-up monomer added to the recycle stream. Conventional gas phase polymerizations are disclosed, for example, in U.S. Pat. Nos. 3,922,322; 4,035,560; and 4,994,534. Optionally, and preferably, a conventional polymerization of the present invention is conducted in the presence of one or more inert particulate materials as described in U.S. Pat. No. 4,994,534.

Condensed mode polymerizations are disclosed in U.S. Pat. Nos. 4,543,399; 4,588,790; 4,994,534; 5,352,749; and 5,462,999. Condensing mode processes are employed to achieve higher cooling capacities and, hence, higher reactor productivity. In these polymerizations a recycle stream, or a portion thereof, can be cooled to a temperature below the dew point in a fluidized bed polymerization process, resulting in condensing all or a portion of the recycle stream. The recycle stream is returned to the reactor. The dew point of the recycle stream can be increased by increasing the operating pressure of the reaction/recycle system and/or increasing the percentage of condensable fluids and decreasing the percentage of non-condensable gases in the recycle stream. The condensable fluid may be inert to the catalyst, reactants and the polymer product produced; it may also include monomers and comonomers. The condensing fluid can be introduced into the reaction/recycle system at any point in the system. Condensable fluids include saturated or unsaturated hydrocarbons. In addition to condensable fluids of the polymerization process itself, other condensable fluids, inert to the polymerization can be introduced to "induce" condensing mode operation. Examples of suitable condensable fluids may be selected from liquid saturated hydrocarbons containing 2 to 8 carbon atoms (e.g., ethane, propane, n-butane, isobutane, n-pentane, isopentane, neopentane, n-hexane, isohexane, and other saturated C6 hydrocarbons, n-heptane, n-octane and other saturated C7 and C8 hydrocarbons, and mixtures thereof). Condensable fluids may also include polymerizable condensable comonomers such as olefins, alpha-olefins, diolefins, diolefins containing at least one alpha olefin, and mixtures thereof. In condensing mode, it is desirable that the liquid entering the fluidized bed mode is dispersed and vaporized quickly.

Liquid monomer polymerization mode is disclosed in U.S. Pat. No. 5,453,471; U.S. Ser. No. 510,375; PCT 95/09826 (US) and PCT 95/09827 (US). When operating in the liquid monomer mode, liquid can be present throughout the entire polymer bed provided that the liquid monomer present in the bed is adsorbed on or absorbed in solid particulate matter present in the bed, such as in/on polymer being produced or fluidization aids, also known as inert particulate materials (e.g., carbon black, silica, clay, talc, and mixtures thereof) present in the bed, so long as there is no substantial amount of free liquid monomer present. Liquid mode makes it possible to produce polymers in a gas phase reactor using monomers having condensation temperatures much higher than the temperatures at which conventional polyolefins are produced.

In general, a liquid monomer process is conducted in a stirred bed or gas fluidized bed reaction vessel having a polymerization zone containing a bed of growing polymer particles. The process comprises continuously introducing a stream of monomer (1,3-butadiene) and optionally one or more inert gases into the polymerization zone optionally in the presence of one or more inert particulate materials; continuously or intermittently introducing a catalyst as described herein into the polymerization zone; continuously or intermittently withdrawing polymer product from the polymerization zone; and continuously withdrawing unreacted gases from the zone; compressing and cooling the gases while maintaining the temperature within the zone below the dew point of at least one monomer present in the zone. Since there is only one monomer present in the gas-liquid stream, there is also present at least one inert gas. The inert gas can include nitrogen, argon, a $C_1$–$C_{20}$ alkane, and mixtures thereof, with nitrogen, butane, or a mixture of these two being preferred. Typically, the temperature within the zone and the velocity of gases passing through the zone are such that essentially no liquid is present in the polymerization zone that is not adsorbed on or absorbed in solid particulate matter. The use of fluidization aids is preferred in the liquid monomer process and in the process of the present invention. In view of the dew points or condensation temperatures of the monomer employed in the gas phase polymerization process of the present invention, liquid monomer mode is the preferred polymerization mode.

In general, sticky polymers such as EPRs, polybutadiene (e.g., high cis 1,4-polybutadiene), and polyisoprene are produced in a gas-phase fluidized reactor at or above the softening or sticking temperature of the polymer product optionally and preferably in the presence of an inert particulate material selected from the group consisting of carbon black (including modified and treated carbon black), silica, clay, talc, activated carbon, and mixtures thereof. Of the inert particulate materials, carbon black, silica, and a mixture thereof are preferred, with carbon black being most preferred. The inert particulate material is employed in the gas-phase polymerization in an amount ranging from about 0.3 to about 80 weight percent, preferably about 5 to about 75 weight percent, most preferably 5 to 50 weight percent based on the weight of the final elastomeric polymer product. Other inert particulate materials (especially carbon blacks) that can be employed are disclosed in U.S. Pat. Nos. 5,162,463 and 5,200,477; WO 98/34960; U.S. Ser. Nos. 09/342,706 (D-17851) and 09/343,169 (D-17945).

Generally, all of the above modes of polymerizing are carried out in a gas phase fluidized bed made up of or containing a "seed bed" of polymer which is the same or different from the polymer product being produced. The bed is preferably made up of the same granular resin that is to be produced in the reactor. Thus, during the course of the polymerization, the bed comprises formed polymer particles, growing polymer particles, and catalyst particles fluidized by polymerizing and modifying gaseous components introduced at a flow rate or velocity sufficient to cause the particles to separate and act as a fluid.

The fluidizing gas is made up of the initial feed, make-up feed, and cycle (recycle) gas, i.e., monomers, and, if desired, modifiers and/or an inert carrier gas (e.g., nitrogen, argon, or inert hydrocarbon (e.g., a $C_{1-C20}$ alkane such as ethane or butane), with nitrogen and/or butane being preferred). A typical cycle gas is comprised of one or more monomers, inert carrier gas(es), and optionally hydrogen, either alone or in combination. The process can be carried out in a batch or continuous manner, the latter being preferred. The essential parts of the reactor are the vessel, the bed, the gas distribution plate, inlet and outlet piping, at least one compressor, at least one cycle gas cooler or heat exchanger, and a product discharge system. In the vessel, above the bed, there is a velocity reduction zone, and in the bed, a reaction zone. Both are above the gas distribution plate.

Variations in the reactor can be introduced if desired. One involves the relocation of one or more cycle gas compressors from upstream to downstream of the cooler and another involves the addition of a vent line from the top of the product discharge vessel (stirred tank product) back to the top of the reactor to improve the fill level of the product discharge vessel.

Polymerization can also be conducted by charging one monomer initially, allowing it to polymerize, and then adding a second monomer, and allowing it to polymerize in a single polymerization vessel. Alternatively, two or more polymerization vessels, preferably connected in series, can be used to polymerize with two or more monomers. Using multiple reactors, one monomer can be polymerized in the first reactor, and additional monomers can be polymerized in second or subsequent reactors.

In general the polymerization conditions in the gas phase reactor are such that the temperature ranges from about 0° to 120° C., preferably about 40° to 100° C., and most preferably about 50° to 80° C. Partial pressure will vary depending upon the particular monomer employed and the temperature of the polymerization, and it can range from about 1 to 125 psi. Condensation temperatures of the monomers are well known. In general, it is preferred to operate at a partial pressure slightly above to slightly below (that is, ±10 psi) the dew point of the monomer. For example, for butadiene and isoprene-butadiene, the partial pressure ranges from about 10 to about 100 psi; and isoprene partial pressure ranges from about 10 to about 50 psi. For an isoprene polymerization in liquid monomer mode the liquid monomer (isoprene) is maintained at a concentration of about 1 to about 30 wt % of isoprene monomer to polymer in the reactor. Total reactor pressure ranges from about 100 to about 500 psi. Though not a diene, styrene is polymerized analogous to other diene polymerizations such as those of butadiene or ethylidene norbornene. Typically, the process of this invention is operated to have a space-time-yield ratio (STY) of about 1:10. That is, they generally require a longer residence time than alpha olefin polymerizations. The higher the space-time-yield ratio the faster the polymer product is produced in the reactor.

Polymers.

Polymers which can be benefited by the present invention are preferably granular. They can include polyolefins or alpha olefins such as, for example, homopolymers of ethylene or propylene, copolymers and terpolymers of a major mole percent of ethylene and/or propylene as the main monomer(s) and a minor mole percent of at least one C3 to C8 alpha olefin; a sticky polymer; as well as polyvinyl chlorides; and elastomers such as polybutadiene, EPMs, EPDMs, polyisoprene, styrene, and vinylpolybutadiene. The preferred C3 to C8 alpha olefins are propylene, butene-1, pentene-1, hexene-1, 4-methylpentene-1, heptene-1, and octene-1. This description is not intended to exclude the use of this invention with alpha olefin homopolymer and copolymer resins in which ethylene is not a monomer. Examples of sticky polymers which can be benefited by the present invention include ethylene-propylene rubbers and ethylene-propylene-diene rubbers, polybutadiene, polyisoprene, high ethylene content propylene/ethylene block copolymers, poly (1-butene) (when produced under certain conditions), very low density (low modulus) polyethylenes, i.e., ethylen butene rubbers or hexene containing terpolymers, ethylene/propylene/ethylidene norbornene, ethylene/propylen/octadiene, and ethylene/propylene/hexadiene terpolymers.

All references cited herein are incorporated by reference. The invention is illustrated by the examples which follow. All parts and percentages in the specification are by weight unless otherwise specified.

What is claimed:

1. An apparatus comprising:
   (1) a pressure rated sampling vessel with a conical discharge bottom having a cone angle of at least 45° to prevent sticky solids from bridging the bottom of the vessel;
   (2) one or more filters to keep a solid product inside the sampling vessel and prevent said solid product from migrating to instrumentation or to one or more process streams;
   (3) one or more full-bore PLC-controlled remotely actuated valves connected to a reactor, that minimize leaks from the reactor into the sampling vessel;
   (4) one or more PLC-controlled remotely actuated valves connecting the sampling vessel to other process streams comprising purge gas, quench agent, vent, flare, reactor cycle gas, or to discharge the product;
   (5) a programmable logic controller (PLC) connecting the PLC-controlled remotely actuated valves and the sample vessel, which sequences the operation of the PLC-controlled remotely actuated valves and performs logic tests in conjunction with one or more process instrumentation devices including pressure, temperature, and flow sensors ensuring the apparatus is operating safely and is performing requested functions; and
   (6) a manual discharge isolation valve coupling a sample container and the sample vessel which allows control of a final discharge of the product into the sample container of off-line analysis.

2. The apparatus of claim 1, wherein there are two full-bore PLC-controlled remotely actuated valves.

3. The apparatus of claim 1, wherein the sampling vessel is pressure rated to 600 psig.

4. The apparatus of claim 1, wherein the full-bore PLC-controlled remotely actuated valves are ball valves.

5. The apparatus of claim 1, wherein the PLC-controlled remotely actuated valves are ball valves.

6. The apparatus of claim 1, wherein the manual discharge isolation valve is a full-bore valve.

7. The apparatus of claim 6, wherein the manual discharge isolation valve is a ball valve.

8. The apparatus of claim 1, wherein one of the PLC-controlled remotely actuated valves is a three-way valve.

9. The apparatus of claim 1, wherein the solid product is a polymer.

10. The apparatus of claim 1, wherein the filter is a sintered metal filter media with a pore size ranging from about 1 to about 10 microns.

* * * * *